(12) United States Patent
Ashtarolnakhai

(10) Patent No.: US 11,839,723 B2
(45) Date of Patent: Dec. 12, 2023

(54) SYSTEM, METHOD, AND APPARATUS FOR DETECTING TUBE MISPLACEMENT IN A PATIENT'S AIRWAY

(71) Applicant: Avent, Inc., Alpharetta, GA (US)

(72) Inventor: Shadi Ashtarolnakhai, Sandy Springs, GA (US)

(73) Assignee: Avent, Inc., Alpharetta, GA (US)

( * ) Notice: Subject to any disclaimer, the term of this patent is extended or adjusted under 35 U.S.C. 154(b) by 285 days.

(21) Appl. No.: 16/291,093

(22) Filed: Mar. 4, 2019

(65) Prior Publication Data

US 2020/0282180 A1 Sep. 10, 2020

(51) Int. Cl.
*A61J 15/00* (2006.01)
*A61M 25/01* (2006.01)

(52) U.S. Cl.
CPC ...... *A61M 25/0105* (2013.01); *A61J 15/0003* (2013.01); *A61J 15/0084* (2015.05); *A61M 2025/0166* (2013.01); *A61M 2205/3313* (2013.01); *A61M 2205/50* (2013.01); *A61M 2230/432* (2013.01)

(58) Field of Classification Search
CPC ... A61B 5/065; A61J 15/0003; A61J 15/0084; A61M 2230/432
See application file for complete search history.

(56) References Cited

U.S. PATENT DOCUMENTS

| 4,836,214 A | 6/1989 | Sramek |
| 4,921,481 A | 5/1990 | Danis et al. |
| 5,193,544 A * | 3/1993 | Jaffe ............... A61B 5/1459 128/207.14 |
| 5,423,320 A * | 6/1995 | Salzman ........... A61B 5/1459 600/473 |

(Continued)

FOREIGN PATENT DOCUMENTS

| CN | 108159541 A | 6/2018 |
| WO | WO 92/17150 | 10/1992 |

OTHER PUBLICATIONS

Chowdhurya, et al. MEMS Infrared Emitter and Detector for Capnography Applications, 2016, Procedia Engineering 168, 1204-1207 1877-7058 (Year: 2016).*

(Continued)

*Primary Examiner* — William R Carpenter
(74) *Attorney, Agent, or Firm* — Dority & Manning, P.A.

(57) ABSTRACT

Tube tip detection systems, enteral tubes, and methods for detecting tube misplacement in a patient's airway are provided. For example, a tube tip detection system comprises an enteral tube having a tip, a first sensing component disposed at the tip, and a feedback display. Feedback from the first sensing component is displayed on the feedback display to indicate to a user of the tube tip detection system whether the tip is misplaced in a patient's airway. Similarly, an enteral tube comprises a tip, a length, and a sensing component. The sensing component is a micro-electro-mechanical system (Continued)

(MEMS) infrared carbon dioxide sensor. Further, a detection method comprises embedding a carbon dioxide sensing component into an enteral tube, inserting the enteral tube into the patient through the patient's nose or mouth, and monitoring feedback from the carbon dioxide sensing component to determine if the enteral tube is traveling into the patient's airway.

11 Claims, 6 Drawing Sheets

(56) References Cited

U.S. PATENT DOCUMENTS

| | | | |
|---|---|---|---|
| 6,334,064 B1 | 12/2001 | Fiddian-Green | |
| 6,357,447 B1 | 3/2002 | Swanson et al. | |
| 6,436,347 B1* | 8/2002 | Cedon | G01N 22/00 |
| | | | 422/56 |
| 7,818,155 B2 | 10/2010 | Stuebe et al. | |
| 8,147,486 B2 | 4/2012 | Honour et al. | |
| 8,613,702 B2 | 12/2013 | Feer et al. | |
| 8,986,230 B2 | 3/2015 | Nishtala | |
| 9,179,971 B2 | 11/2015 | Kirschenman | |
| 9,226,878 B2 | 1/2016 | Elia et al. | |
| 9,295,395 B2 | 3/2016 | Elia et al. | |
| 9,532,739 B2 | 1/2017 | Bennett-Guerrero | |
| 9,610,227 B2 | 4/2017 | Elia | |
| 9,642,779 B2 | 5/2017 | Elia et al. | |
| 9,713,579 B2 | 7/2017 | Elia et al. | |
| 2003/0060764 A1* | 3/2003 | Dua | A61M 1/84 |
| | | | 604/129 |
| 2007/0175769 A1* | 8/2007 | Hsiung | G01N 27/4162 |
| | | | 204/424 |
| 2007/0261698 A1* | 11/2007 | Palatnik | A61B 5/742 |
| | | | 128/207.14 |
| 2008/0097179 A1 | 4/2008 | Russo | |
| 2008/0167607 A1 | 7/2008 | Pfeiffer et al. | |
| 2008/0249467 A1 | 10/2008 | Burnett et al. | |
| 2009/0209849 A1 | 8/2009 | Rowe et al. | |
| 2009/0275825 A1* | 11/2009 | Thomas | A61J 15/0088 |
| | | | 600/424 |
| 2012/0016256 A1 | 1/2012 | Mabary et al. | |
| 2012/0277619 A1 | 11/2012 | Starkebaum et al. | |
| 2013/0225946 A1 | 8/2013 | Feer et al. | |
| 2016/0113843 A1 | 4/2016 | Elia et al. | |
| 2016/0129223 A1 | 5/2016 | Kirschenman | |
| 2016/0206189 A1 | 7/2016 | Nearman et al. | |
| 2016/0331298 A1 | 11/2016 | Burnett et al. | |
| 2017/0071502 A1 | 3/2017 | Bennett-Guerrero | |
| 2017/0202750 A1 | 7/2017 | Elia | |
| 2018/0078195 A1* | 3/2018 | Sutaria | A61B 7/00 |
| 2018/0161249 A1 | 6/2018 | Elia et al. | |
| 2018/0289536 A1 | 10/2018 | Burnett | |
| 2019/0070347 A1* | 3/2019 | Hierold | A61B 5/0215 |

OTHER PUBLICATIONS

Phillips et al, How far to pass a nasogastric tube? Particular reference to the distance from the anterior nares to the upper oesophagus, Journal of the Royal College of Surgeons of Ediburgh, 39(5):295-6 (Year: 1994).*

J.J. Lai et al., "MEMS integrated narrow band infrared emitter and detector for infrared gas sensor", Journal of Physics: Conference Series, vol. 276, Feb. 1, 2011, 4 pages.

International Search Report and Written Opinion for PCT/US2020/018614, dated May 28, 2020, 15 pages.

\* cited by examiner

SYSTEM, METHOD, AND APPARATUS FOR DETECTING TUBE MISPLACEMENT IN A PATIENT'S AIRWAY

FIELD

The present subject matter relates generally to a system, method, and apparatus for administering fluids to body cavities and, more particularly, to such systems, methods, and apparatus utilizing a carbon dioxide sensor to detect whether a tube is incorrectly inserted into a patient's airway.

BACKGROUND

Physicians and other health care providers frequently use catheters, which include tubes inserted into the human body, to treat patients. A nasogastric (NG) tube is one type of tube that is placed in the gastrointestinal tract for patients experiencing a variety of ailments. NG tubes are placed through the nasal cavity and are intended to traverse through the esophagus down into the stomach and into the small bowel, if desired. As the tube travels through the oropharynx and hypopharynx, the anatomy splits into the trachea and the esophagus. Tubes commonly are misplaced into the trachea, which can result in pneumonia, pneumothoraces, or even death. As such, there is a critical need for a way to determine when the tube has taken the path of the trachea as opposed to the desired path of the esophagus.

In some cases, health care providers use X-ray machines to gather information about the location of the catheters within the body. There are several disadvantages in using X-ray machines. For instance, X-rays from these machines are a known carcinogen, if received in sufficient doses. Also, X-ray machines are relatively large and heavy, consume a relatively large amount of energy, and may expose the patient to a relatively high degree of radiation. Moreover, these machines are typically not readily accessible for use because, due to their size, they are usually installed in a special X-ray room. This room can be relatively far away from the patient's room. Therefore, health care providers may find it inconvenient to use these machines for their catheter procedures. Further, it can be inconvenient to transport these machines to a patient's home for home care catheter procedures. As such, X-ray confirmation of the tube tip position may be performed only when the position is uncertain, and the enteral tube position more commonly is checked by assessing the pH of tube aspirate. However, it can be difficult to determine a practical pH cutoff level for reliable confirmation of NG tube placement, particularly for pediatric patients.

In other cases, electromagnetism is used to monitor the location or position of the enteral tube tip. For example, an electromagnetic stylet inserted into the patient's body with the enteral tube may provide real-time location information on the tube tip placement within a patient's anatomy. A receiver unit outside the body detects an electromagnetic field transmitted by the stylet and provides on-screen visualization and, thereby, immediate feedback on tube placement. Nevertheless, due to, e.g., variation in placement of the receiver unit and user misinterpretations of the feedback from the electromagnetic stylet, a health care provider can fail to recognize a misplacement of the enteral tube tip within the patient's airway.

Thus, recognition of the airway when placing an enteral tube is an important way to prevent harm to a patient, and the art is continuously seeking new and improved systems, apparatus, and methods for determining a location of a tip of a catheter, such as an NG tube, being inserted into a patient. For instance, an improved enteral tube, such as an NG tube, incorporating means for detecting carbon dioxide to determine whether the enteral tube is being improperly inserted in a patient's airway would be useful. More particularly, embedding one or more $CO_2$ sensors in an enteral tube, such as an NG tube, for detecting the $CO_2$ concentration along the path of the tube would be desirable. Further, incorporating a micro-electro-mechanical system (MEMS) that detects $CO_2$ in a range of the CO2 concentration in a person's exhaled breath into, e.g., the tip of the enteral tube would be useful. Additionally, systems for conveying feedback from such carbon dioxide sensors to a health care provider would be beneficial. Moreover, methods for detecting a tube misplacement in a patient's airway utilizing such carbon dioxide sensors would be advantageous.

SUMMARY

Objects and advantages of the invention will be set forth in part in the following description, or may be obvious from the description, or may be learned through practice of the invention.

In one aspect, the present subject matter is directed to a tube tip detection system that comprises an enteral tube having a tip, a first sensing component disposed at the tip, and a feedback display. Feedback from the first sensing component is displayed on the feedback display to indicate to a user of the tube tip detection system whether the tip is misplaced in a patient's airway. It should also be understood that the system may further include any of the additional features as described herein.

In another aspect, the present disclosure is directed to an enteral tube that comprises a tip, a length, and a sensing component. The sensing component is a micro-electro-mechanical system (MEMS) infrared carbon dioxide sensor. It should also be appreciated that the enteral tube may further include any of the additional features as described herein.

In yet another aspect, the present disclosure is directed to a method for detecting a tube misplacement in a patient's airway. The method comprises embedding a carbon dioxide sensing component into an enteral tube, inserting the enteral tube into the patient through the patient's nose or mouth, and monitoring feedback from the carbon dioxide sensing component to determine if the enteral tube is traveling into the patient's airway. It should also be understood that the method may further include any of the additional features as described herein.

These and other features, aspects and advantages of the present subject matter will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present subject matter, including the best mode thereof, directed to one of ordinary skill in the art, is set forth in the specification, which makes reference to the appended figures, in which.

DETAILED DESCRIPTION

Figure 1A:
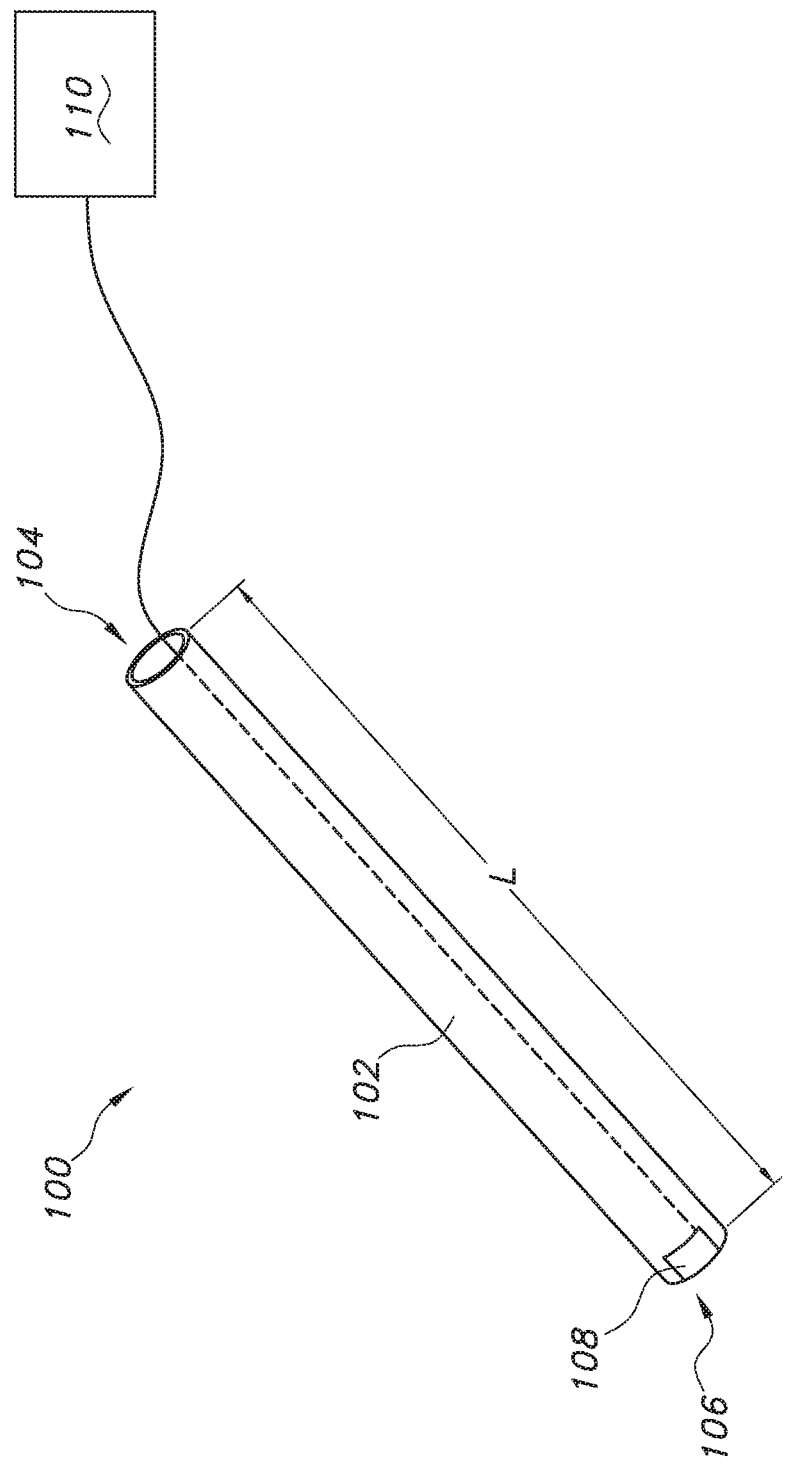
FIG. 1A provides a schematic view of a tube tip detection system having an enteral tube, a sensing component embedded in the enteral tube, and a feedback display, according to an exemplary embodiment of the present subject matter.

Reference will now be made in detail to one or more embodiments of the invention, examples of the invention, examples of which are illustrated in the drawings. Each example and embodiment is provided by way of explanation of the invention, and is not meant as a limitation of the invention. For example, features illustrated or described as part of one embodiment may be used with another embodiment to yield still a further embodiment. It is intended that the invention include these and other modifications and variations as coming within the scope and spirit of the invention.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Generally, the present subject matter provides catheters for intubating patients having one or more sensing components for sensing carbon dioxide to determine, using the carbon dioxide concentration sensed by the sensing component(s), whether the catheter is being inserted into the patient's airway. Certain catheters are inserted into through the patient's nose or mouth and extend into the patient's gastrointestinal tract and, thus, also may be referred to as enteral catheters or enteral tubes. More particularly, enteral tubes inserted through the patient's nose are called nasogastric (NG) tubes, which typically are feeding tubes. The feeding tube tip, through which a fluid flows into the patient, is disposed in the stomach or intestines, and a feeding source delivers liquid nutrient, liquid medicine, or a combination of the two to the patient. Because erroneous placement of the tube tip may injure or harm the patient, particularly if the tube is misplaced into the patient's airway, it is important to place the tip of the tube at the proper location within the patient's body. Thus, the present subject matter provides enteral tubes having one or more carbon dioxide sensors, which continuously sense carbon dioxide as the enteral tube is inserted into a patient such that a user (such as a health care provider) can determine whether the enteral tube is being misplaced into the patient's airway, where the carbon dioxide concentration is increased compared to the carbon dioxide concentration in the correct placement area, the patient's esophagus and gastrointestinal tract. Further, the present subject matter provides systems and methods for detecting a tube misplacement in a patient's airway.

Figure 1B:
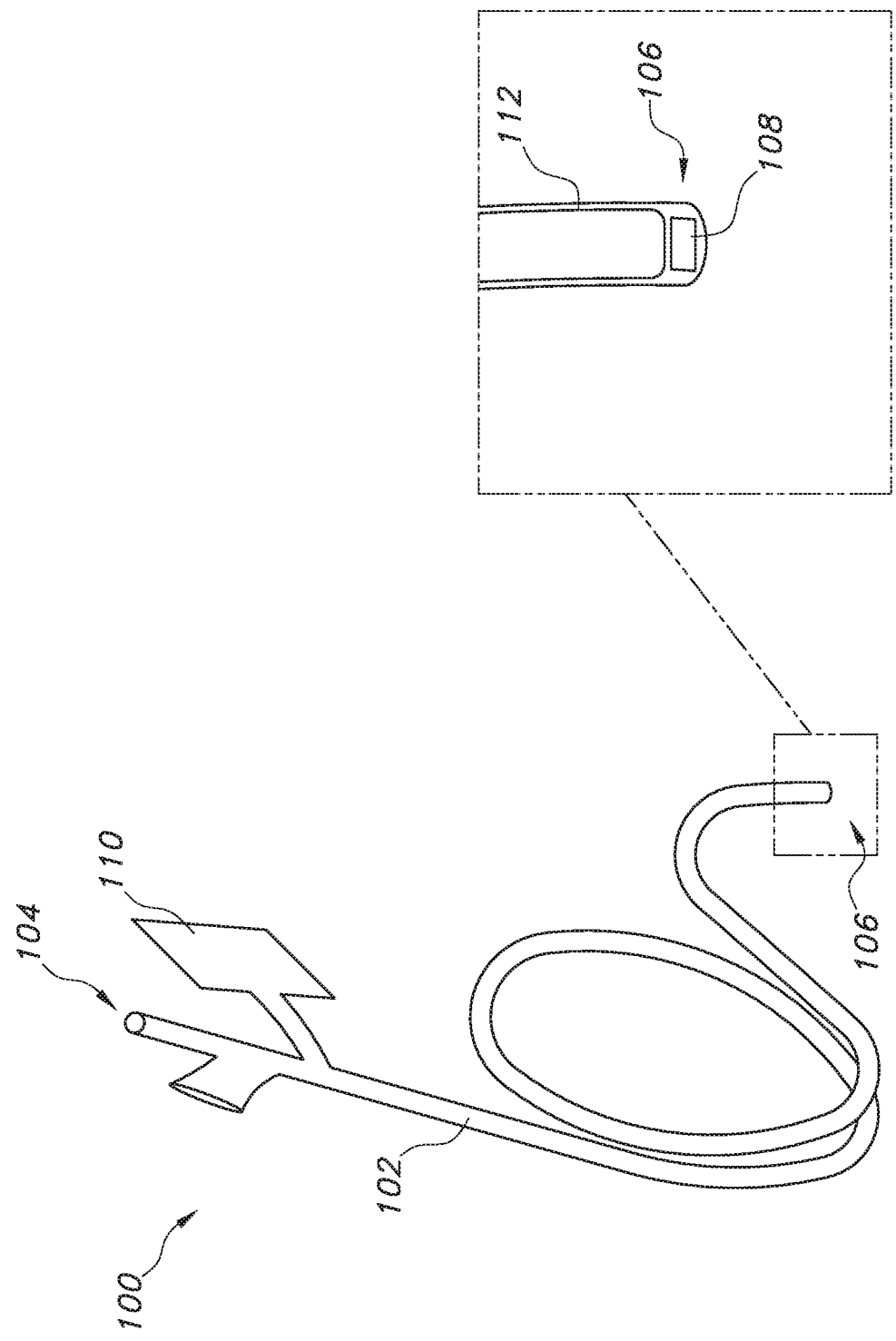
FIG. 1B illustrates the tube tip detection system of FIG. 1A and provides an enlarged view of a tip of the enteral tube.

Referring now to the drawings, FIGS. 1A and 1B illustrates a tube tip detection system 100 having an enteral tube 102 that includes a proximal end or head 104 and a distal end or tip 106. The enteral tube 102 has a length L between the proximal end 104 and the tip 106. Further, the enteral tube 102 should have an appropriate diameter and be sufficiently flexible for insertion through, e.g., a patient's nose or mouth and into the patient's gastrointestinal tract. For instance, the enteral tube 102 should have a size within a range of five to seven French (5 Fr to 7 Fr) for pediatric patients and within a range of ten to twelve French (8 Fr to 12 Fr) for adult patients.

In exemplary embodiments the enteral tube 102 is a nasogastric (NG) tube, which, through a process called nasogastric intubation, is inserted through a patient's nose into the patient's stomach. In other exemplary embodiments, the enteral tube 102 is an orogastric (OG) tube inserted during orogastric intubation through the patient's mouth into the stomach. Alternatively, the tube tip 106 may extend into the patient's intestines rather than the stomach. Whether the tip 106 is disposed in the stomach or intestines may depend on, e.g., the specific needs of the patient. For typical nasogastric intubations or orogastric intubations, the tube tip 106 should be in a sub-diaphragmatic position in the stomach, e.g., at least ten (10) centimeters (cm) beyond the gastro-esophageal junction (GOJ), also known as the oesophagogastric junction, which is the part of the gastrointestinal tract where the esophagus and stomach are joined.

As discussed herein, misplacement of the tip 106 in the patient's airway, e.g., the bronchi or the lungs, rather than in the patient's gastrointestinal tract is a complication of nasogastric or orogastric intubation. To avoid such misplacement, the present subject matter provides enteral tubes 102 with sensing components to detect whether the tube tip 106 is being misplaced in the patient's airway. In the depicted embodiment, a first sensing component 108 is disposed at the tip 106, and a feedback display 110 is disposed at the head 104. In exemplary embodiments, the first sensing component 108 is a micro-electro-mechanical system (MEMS) component, which provides a miniaturized sensor having appropriate dimensions to be embedded in a wall 112 of enteral tube 102 at its tip 106. More specifically, silicon-based MEMS sensors can be fabricated in small sizes, such as in micrometer ($\mu m$) to millimeter (mm) sizes, in clean rooms and then embedded in enteral tubes 102. Feedback from the first sensing component 108 is displayed on the feedback display 110 to indicate to a user of the tube tip detection system 100 whether the tip 104 is misplaced in a patient's airway or is properly placed in the patient's esophagus or gastrointestinal tract. The user may be a health care provider, such as a physician, clinician, nurse, etc.

The MEMS component 108 includes one or more MEMS active and passive components that form a non-dispersive infrared (IR) sensor. Carbon dioxide ($CO_2$) strongly absorbs infrared radiation at a wavelength of 4.3 $\mu m$. Further, the $CO_2$ concentration at the end of a person's exhaled breath is approximately 5% to 6% of the exhaled air, which corresponds to about 35 mmHg to about 45 mmHg. Therefore, the MEMS infrared sensor is configured to detect $CO_2$ to determine whether the enteral tube is being misplaced in the patient's airway and may be referred to as a MEMS infrared carbon dioxide sensor 108. More particularly, the MEMS component 108 includes an IR emitter 108a and an IR receiver 108b, which form the MEMS infrared carbon dioxide sensor 108. The IR emitter 108a emits infrared radiation, and the IR receiver 108b receives any reflected radiation. An IR path length between the IR emitter 108a and the IR receiver 108b dictates the $CO_2$ concentration the IR carbon dioxide sensor 108 can detect. Thus, the MEMS component 108, particularly the IR emitter 108a and IR receiver 108b, should be constructed such that the sensor 108 can detect a $CO_2$ concentration of at least 30 mmHg to 50 mmHg and, in particular embodiments, of at least 35 mmHg to 45 mmHg.

Based on the reflected IR radiation, the tube tip detection system 100 determines how much IR radiation was absorbed by the air surrounding the enteral tube 102 and thereby determines the $CO_2$ concentration of the air within a pathway 114 (FIG. 4) being traversed by the tube 102. In some embodiments, if the $CO_2$ concentration is at least 30 mmHg, the tube tip detection system 100 may determine that the tip 106 of the enteral tube 102 is being misplaced in the patient's airway. In other embodiments, the tube tip detection system 100 may determine that the tip 106 of the enteral tube 102 is being misplaced in the patient's airway if the $CO_2$ concentration is at least 35 mmHg. That is, the first sensing component 108, or MEMS infrared carbon dioxide sensor 108, embedded in the enteral tube 102 near its tip 106 is configured to sense a $CO_2$ concentration of at least 30 mmHg, or in other embodiments, of at least 35 mmHg, which corresponds to the low end of the typical range of $CO_2$ concentration in a person's exhaled breath. When the sensing component 108 senses such a $CO_2$ concentration, the sensing component 108 provides feedback of the $CO_2$ concentration to the user via the feedback display 110. In some embodiments, the feedback from the sensing component 108 indicates the tip 106 is entering the airway when the $CO_2$ concentration sensed by the sensing component 108 is 30 mmHg or 35 mmHg. In other embodiments, if the $CO_2$ concentration continues to rise past 30-35 mmHg as the enteral tube 102 is advanced into the patient, as shown on the feedback display 110, the user may determine that the enteral tube 102 is being incorrectly placed in the patient's airway because the rising $CO_2$ concentration likely corresponds to the patient's respirations conveyed through the patient's airway. Stated differently, using the $CO_2$ level or concentration that is detected by the first sensing component 108, the user can determine whether the enteral tube tip 106 resides in the patient's airway.

Figure 2:
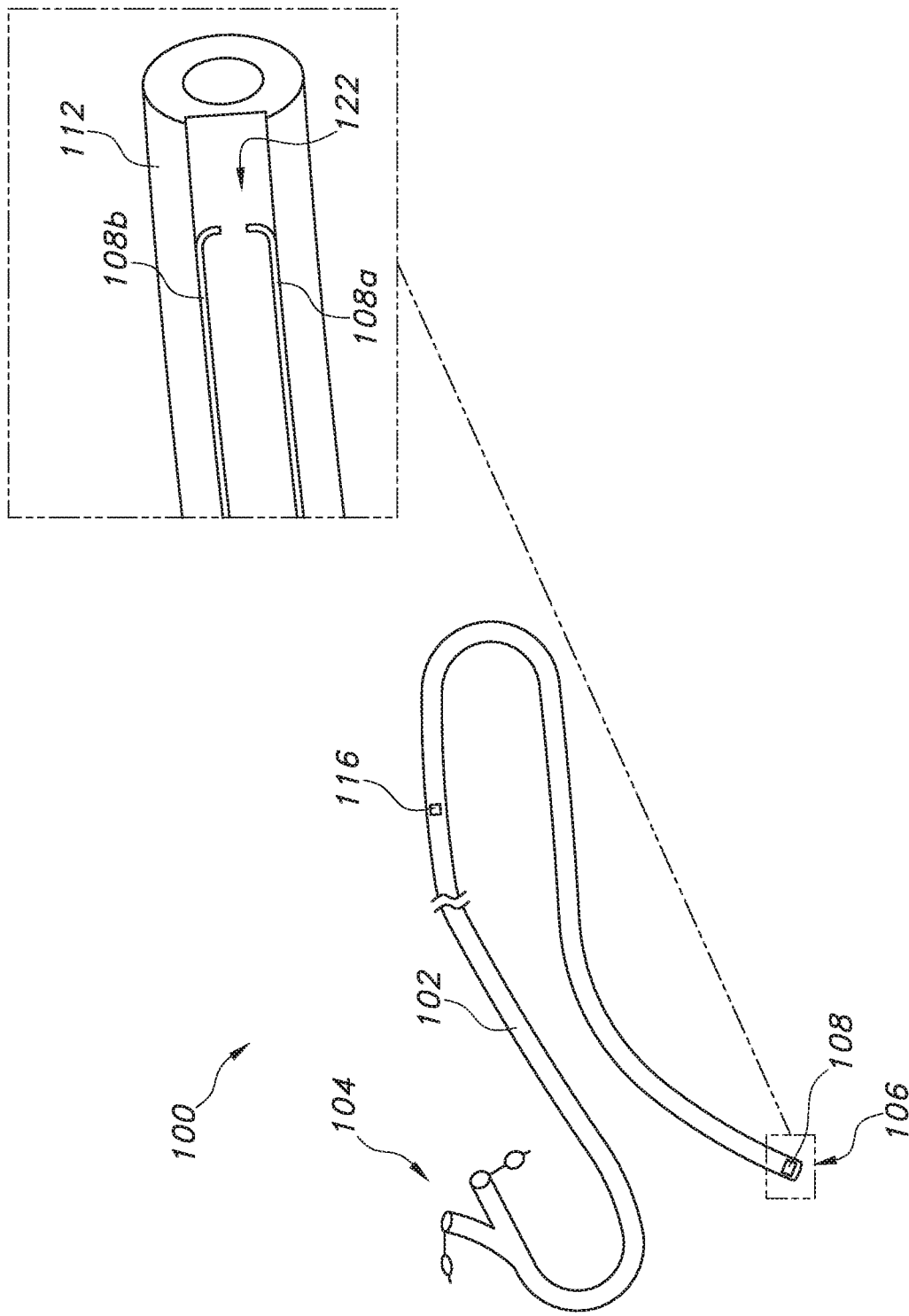
FIG. 2 illustrates a tube tip detection system according to another exemplary embodiment of the present subject matter, the system having an enteral tube and more than one sensing component embedded in the enteral tube.
Figure 3:
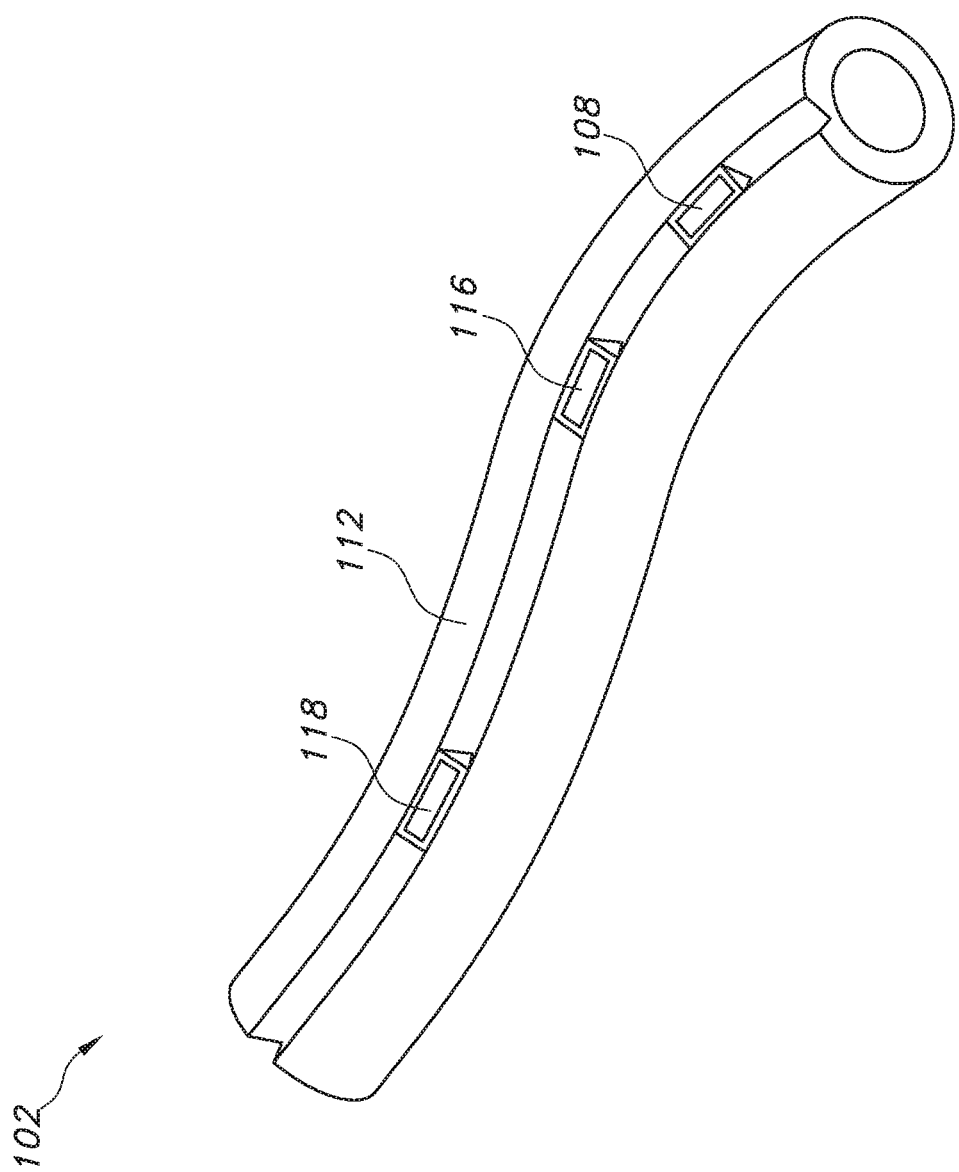
FIG. 3 provides a side perspective view of a portion of an enteral tube having a plurality of sensing components disposed in a channel formed in a wall of the enteral tube.

FIGS. 2 and 3 illustrate other exemplary embodiments of the tube tip detection system 100. As shown, in some embodiments, the enteral tube 102 includes a plurality of sensing components that are spaced apart from one another along the length L of the tube 102. As described above, each sensing component of the plurality of sensing components is a carbon dioxide sensor for detecting the $CO_2$ concentration in the air along the pathway traversed by the enteral tube 102 through the patient. More particularly, the embodiment illustrated in FIG. 2 comprises the first sensing component 108 disposed at the tube tip 106 and a second sensing component 116 disposed along the length L at a position spaced apart from the tip 106. For example, the second sensing component 116 may be disposed at a midpoint of the tube length L, i.e., halfway between the proximal end 104 and the tip 106. In other embodiments, such as depicted in FIG. 3, a third sensing component 118 also is disposed along the tube length L at a position spaced apart from the tip 106.

As shown in FIG. 3, to embed the sensing components 108, 116, and/or 118 in the enteral tube 102, in some embodiments a channel 122 is defined in the tube 102 during fabrication of the tube 102. Then, the first sensing component 108, the second sensing component 116, and/or the third sensing component 118 is disposed within the channel 122. Next, a filler material (not shown) is disposed within the channel 122 around the first, second, and/or third sensing components 108, 116, 118 such that the sensing component(s) 108, 116, 118 are embedded within the enteral tube 102. The sensing components 108, 116, 118 may be embedded within the tube 102 in other ways as well.

In some embodiments, like the exemplary embodiment of FIG. 3, the first sensing component 108, the second sensing component 116, and the third sensing component 118 are unequally spaced apart from one another. That is, the distance, or portion of the tube length L, between the first and second sensing components 108, 116 is different from the distance between the second and third sensing components 116, 118. In other embodiments, the first sensing component 108, the second sensing component 116, and the third sensing component 118 are equidistant from one another, i.e., the distance between the first and second sensing components 108, 116 is the same as the distance between the second and third sensing components 116, 118. Also as illustrated in FIG. 3, in some embodiments the first sensing component 108 may not be disposed at the tip 106 of the enteral tube 102 but may be disposed along the tube length L such that the first sensing component 108 is spaced apart from the tip 106. In such embodiments, no sensing component may be disposed at the tip 106; that is, in some embodiments of the tube tip detection system 100, one or more sensing components are disposed on the tube 102 at a distance from the tube tip 106, with no sensing component disposed right at the tip 106. Thus, a variety of placements or positions for the one or more sensing components may be used in various embodiments of the tube tip detection system 100.

Figure 4:
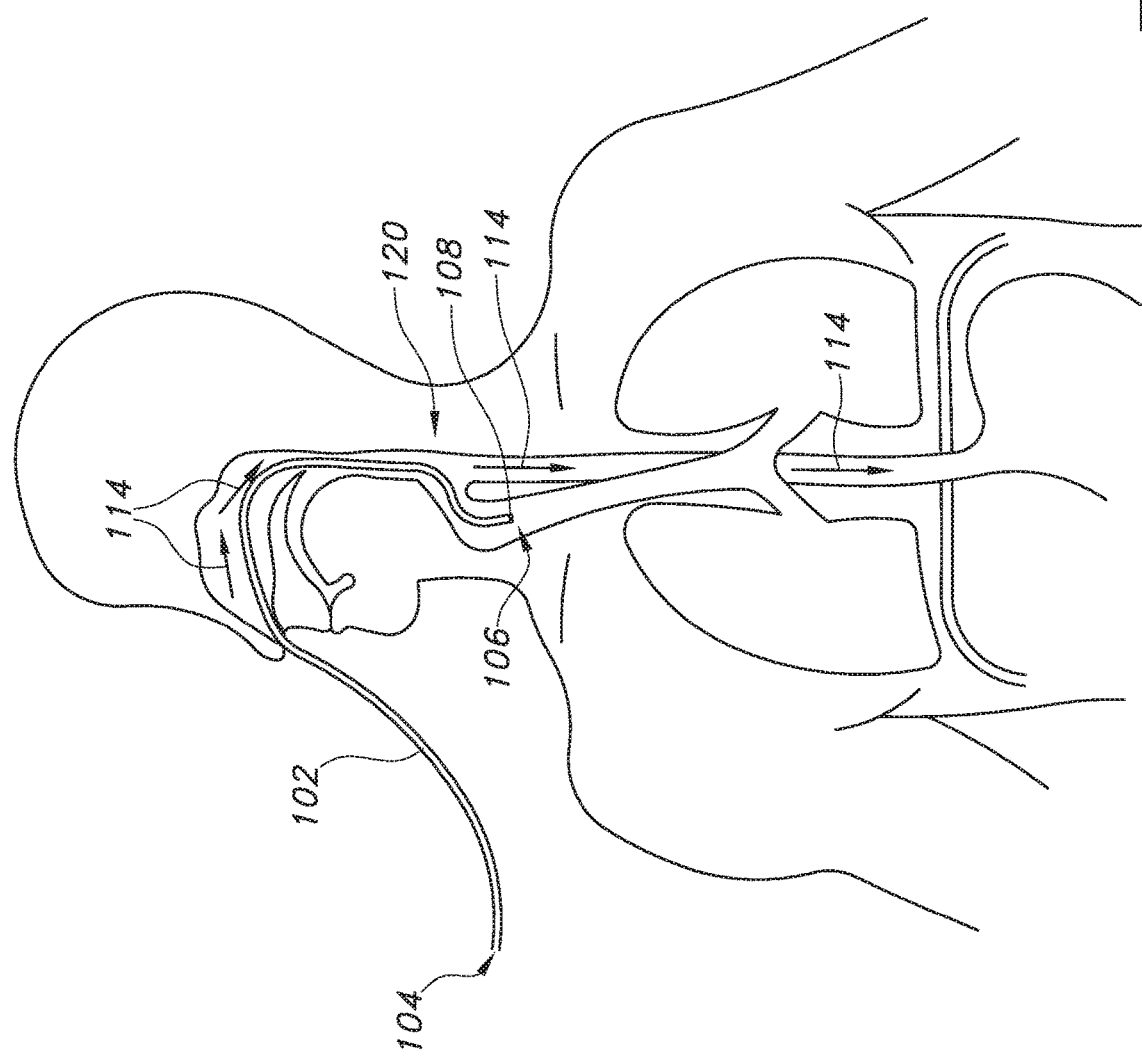
FIG. 4 provides a schematic view of a human patient with a tip of an enteral tube entering the patient's airway and a sensing component disposed at or near the tip to detect that the tip is entering the patient's airway.

Further, in exemplary embodiments, each of the first, second, and third sensing components 108, 116, 118 is a MEMS infrared carbon dioxide sensor. The miniaturized sensors located on the tip 106 and/or other locations of the enteral tube 102 detect a $CO_2$ pattern in the air within the passage traversed by the tube 102. Because the enteral tube 102 has a known length L, the $CO_2$ pattern (a waveform, as the $CO_2$ concentration rises and falls with the patient's respirations, typically three (3) to four (4) respirations per minute) determines if the tube 102 has deviated to the patient's airway. Stated differently, the amount or length of the enteral tube 102 that has been inserted into the patient together with the $CO_2$ concentration detected by the sensor(s) 108, 116, 118 convey to a user of the tube tip detection system 100 whether the tube tip 106 is near the patient's airway and is possibly entering the patient's airway rather than continuing down the pathway toward the patient's stomach or intestines, the intended destination of the tube tip 106. For example, it is known that bifurcation of the pathway 114 into the esophagus and the trachea, as illustrated in FIG. 4, occurs at a certain distance from the entrance to the nostril in a patient, with the certain distance varying between pediatric and adult patients. Knowing this distance for a given patient, as well as the length L of the enteral tube 102, the user can determine how much (or what length) of the tube 102 has been inserted into the patient and, thus, know whether the tube tip 106 is at or near the point where the trachea branches off from the pathway 114, from which the tube 102 could be misplaced into the patient's airway.

As an example, bifurcation typically occurs around 18-20 cm from the entrance to the nostril in adults; the area where bifurcation occurs may be referred to as a bifurcation zone 120, which is depicted in FIG. 4. Thus, for nasogastric intubation of an adult patient, if the $CO_2$ concentration begins to increase when approximately 18 cm of the length L of the enteral tube 102 has been inserted into the patient, the user of the system 100 can conclude that the tube tip 106 is at or near the bifurcation zone 120. If the $CO_2$ concentration continues to increase as the tube 102 is further inserted, the user may determine that the tube tip 106 is or has entered the patient's airway and can correct the tube's position within the patient before continuing to insert the tube 102. If, however, the $CO_2$ concentration does not continue to increase past the bifurcation zone 120, the user may determine that the tube tip 106 is continuing on the correct pathway 114 (i.e., the tube 106 is within the esophagus rather than the trachea) to the patient's stomach or bowel.

Accordingly, the one or more sensing components 108, 116, 118 likely would register, and display on the feedback display 110, an elevated $CO_2$ concentration as the tip 106 of the enteral tube 102 nears the bifurcation zone 120. Thus, the user should monitor the $CO_2$ pattern to distinguish between an appropriately placed tube tip 106 and a misplaced tube tip 106. The $CO_2$ concentration for an appropriately placed tip 106 should decrease upon further insertion of the tube past the bifurcation zone 120, but the $CO_2$ concentration for a misplaced tip 106 should increase as a greater length of the tube 102 (greater than the length of tube 102 to reach the bifurcation zone 120) is inserted into the patient.

In some embodiments, e.g., as shown in FIG. 1B, the feedback display 110 is attached to the enteral tube 102, but in other embodiments, e.g., as shown in FIG. 1A, the feedback display 110 is separate from and not attached to the enteral tube 102. The feedback display 110 displays the actual $CO_2$ concentration detected by the one or more sensing components 108, 116, 118. Additionally or alternatively, the feedback display 110 displays a non-numerical visual indicator of the $CO_2$ concentration, such as one or more colors, symbols, or words. As an example, the visual indicator may comprise a plurality of light emitting diodes (LEDs), such as green, yellow, and red LEDs. In such embodiments, the feedback display 110 illuminates the green LED(s) if the sensed $CO_2$ concentration is below a typical low value of the $CO_2$ concentration of a person's exhaled breath (e.g., if the $CO_2$ concentration is below 30 mmHg), illuminates the yellow LED(s) if the $CO_2$ concentration is within a typical low range of the $CO_2$ concentration of a person's exhaled breath (e.g., if the $CO_2$ concentration is at or between 30 mmHg to 40 mmHg), and illuminates the red LED(s) if the $CO_2$ concentration increases beyond an initial reading at the low end of typical $CO_2$ concentration in a person's exhaled breath. As another example, the feedback display 110 may illuminate a series of colored or non-colored LEDs or display words or symbols to indicate various states of the sensed $CO_2$ concentration (e.g., below low end, at low end, or increasing beyond low end of typical $CO_2$ concentration of a person's exhaled breath). In still other embodiments, the feedback display 110 may utilize audible feedback, such as one or more beeping or other sounds, in addition to or in lieu of visual feedback to convey to the user of the system 100 $CO_2$ concentration sensed by the one or more sensing components 108, 116, 118 disposed on the enteral tube 102.

Figure 5:
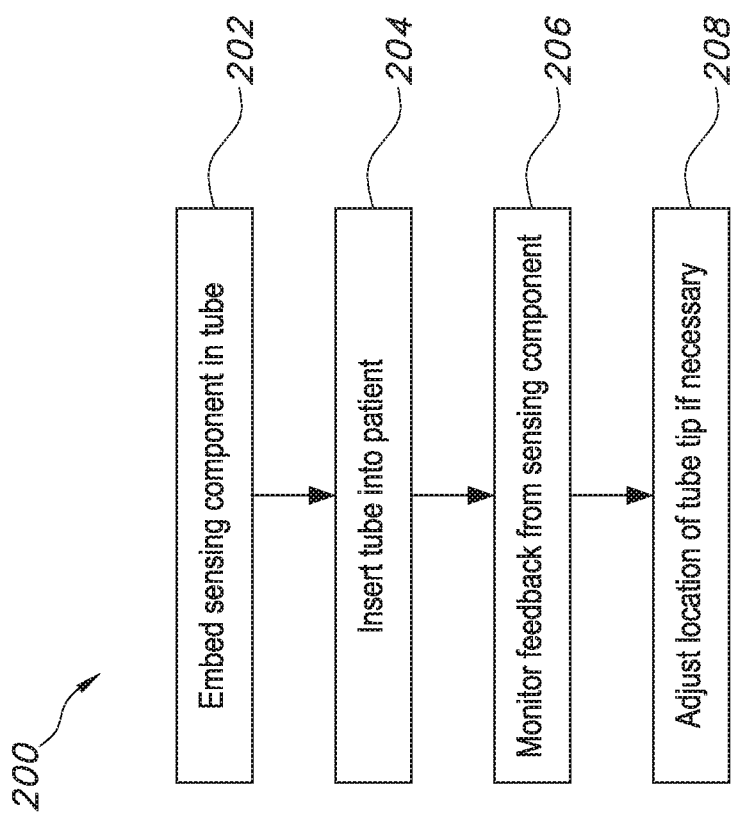
FIG. 5 provides a flow diagram illustrating a method for detecting a tube misplacement in a patient's airway.

The present subject matter also provides methods for detecting a tube misplacement in a patient's airway. Referring now to FIG. 5, an exemplary method 200 is illustrated. The method 200 comprises embedding a carbon dioxide sensing component 108 into an enteral tube 102, as shown at 202 in FIG. 5. The enteral tube 102 is configured as described herein, having a proximal end 104 and a tip 106 separated by a length L of tubing. Moreover, the sensing component 108 may be a MEMS-based infrared carbon dioxide sensor as described above. As shown at 204 in FIG. 5, the method 200 also includes inserting the enteral tube 102 into the patient through the patient's nose or mouth. Thus, the enteral tube 102 may be a nasogastric or orogastric tube as described herein. Further, as shown at 206 and 208 in FIG. 5, the method 200 includes monitoring feedback from the carbon dioxide sensing component 108 to determine if the enteral tube 102 is traveling into the patient's airway and, if so, then adjusting the location of the tube tip 106 such that it is no longer in the patient's airway. The feedback may be displayed on a feedback display 110 as described herein.

It will be appreciated that, in other embodiments, the method 200 may accommodate other configurations of the tube tip detection system 100 as described in greater detail herein. For example, step 202 of the method 200 may comprise embedding a plurality of sensing components into the enteral tube 102, e.g., a first and second sensing component 108, 116 as illustrated in FIG. 2 or a first, second, and third sensing component 108, 116, 118 as illustrated in FIG. 3. Of course, the method 200 may vary to include other configurations of the apparatus and system described herein.

Accordingly, the present subject matter provides a system and apparatus for detecting a tip of an enteral tube as it is inserted into a patient. In exemplary embodiments, the system uses MEMS sensor(s) on the tube to detect elevated levels of $CO_2$ if the tube is inserted into the airway instead of traveling past the bifurcation of the patient's trachea from the patient's esophagus toward the gastrointestinal tract. The system may utilize a single MEMS-based infrared carbon dioxide sensor disposed on the tip of the tube to sense the $CO_2$ concentration within the pathway being traversed by the tube. In other embodiments, the system utilizes a plurality of MEMS-based infrared carbon dioxide sensors disposed along the length of the tube to sense the $CO_2$ concentration within the pathway being traversed by the tube. The system provides feedback to the user of the system, e.g., a physician, clinician, nurse, or other caregiver, via a feedback display or other device for receiving feedback from the one or more sensing components such that the user can determine whether the tube tip is appropriately placed or is misplaced. Methods for detecting whether the tube tip is misplaced also are provided. Such methods, systems, and apparatus can help reduce the occurrence of misplaced enteral tubes, such as nasogastric or orogastric feeding tubes, thereby reducing complications from administering fluid to a patient through a misplaced tube. Further, the methods, systems, and apparatus described herein reduce such misplacements in a cost-efficient and time-efficient manner. More particularly, the carbon dioxide sensors described herein are a relatively low-cost solution and are easily embedded in enteral tubes during the manufacture of the tubes. Moreover, the system described herein allows real-time, bedside verification of the tube placement, which can save time and money, e.g., compared to existing systems that require tube placement to be verified by x-ray or the like. Other benefits and advantages of the present subject matter also may be recognized by those of ordinary skill in the art.

It should also be appreciated that these procedures may involve treatment of humans by physicians, physician assistants, nurses, or other health care providers. In addition, these procedures may involve treatment of other mammals and animals by veterinarians, researchers, and others.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub combination.

Although the present subject matter has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they include structural elements that do not differ from the literal language of the claims or if they include equivalent structural elements with insubstantial differences from the literal language of the claims.

What is claimed is:

1. A tube tip detection system, comprising:
    an enteral tube having a proximal end, a length, a tip, a lumen, and a channel;
    a first sensing component disposed at the tip, the first sensing component comprising a micro-electro-mechanical system (MEMS) component comprising an infrared carbon dioxide sensor having an infrared emitter and an infrared receiver embedded within the channel via a filler material; and
    a feedback display,
    wherein the infrared emitter and the infrared receiver each comprise an end, wherein the end of the infrared emitter and the end of the infrared receive each terminate in a direction that is not parallel with the lumen of the enteral tube,
    wherein the infrared emitter and the infrared receiver define an infrared path length therebetween, the infrared path length configured to detect carbon dioxide concentrations of at least 30 mmHg to 50 mmHg, and
    wherein feedback from the first sensing component is displayed on the feedback display to indicate to a user of the tube tip detection system whether the tip is misplaced in a patient's airway.

2. The tube tip detection system of claim 1, wherein the tube tip detecting system further comprises a second sensing component disposed along the length at a position spaced apart from the first sensing component, wherein a third sensing component is disposed along the length at a position spaced apart from the first and second sensing components.

3. The tube tip detection system of claim 2, wherein the first sensing component, the second sensing component, and the third sensing component are unequally spaced apart from one another.

4. The tube tip detection system of claim 2, wherein the third sensing component is a micro-electrical mechanical system (MEMS) infrared carbon dioxide sensor.

5. The tube tip detection system of claim 1, wherein the feedback display is separate from and not attached to the enteral tube.

6. The tube tip detection system of claim 1, wherein the enteral tube is a nasogastric tube.

7. The tube tip detection system of claim 1, wherein a channel is defined in the enteral tube, wherein the first sensing component is disposed within the channel with a filler material disposed within the channel around the first sensing component to embed the first sensing component within the enteral tube.

8. The tube tip detection system of claim 1, wherein the feedback display comprises a non-numerical visual indicator, wherein the non-numerical visual indicator is plurality of light emitting diodes (LEDs).

9. The tube tip detection system of claim 1, wherein the end of the infrared emitter faces the end of the infrared receiver within the channel of the enteral tube.

10. The tube tip detection system of claim 1, wherein the infrared emitter is disposed on an interior wall of the channel of the enteral tube and the infrared emitter is disposed on an opposite end of the interior wall of the channel of the enteral tube.

11. A method for detecting a tube misplacement in a patient's airway, comprising:
    embedding a first sensing component into an enteral tube, wherein the enteral tube comprises a proximal end, a length, a tip, a lumen, and a channel;
    inserting the enteral tube into the patient through the patient's nose or mouth;
    displaying, on a display, feedback from the first sensing component; and
    monitoring the feedback from the first sensing component to determine if the enteral tube is traveling into the patient's airway, wherein the first sensing component is disposed at the tip and comprises a micro-electro-mechanical (MEMS) component comprising an infrared carbon dioxide sensor having an infrared emitter and an infrared receiver embedded within the channel via a filler material, wherein the infrared emitter and the infrared receiver each comprise an end, wherein the end of the infrared emitter and the infrared receiver each comprise an end, wherein the end of the infrared emitter and the end of the infrared receiver each terminate in a direction that is not parallel with the lumen of the enteral tube, wherein the infrared emitter and the infrared receive define and infrared path length therebetween, the infrared path length configured to detect carbon dioxide concentrations of at least 30 mmHg to 50 mmHg.

* * * * *